United States Patent [19]

Walton et al.

[11] Patent Number: 4,489,065

[45] Date of Patent: Dec. 18, 1984

[54] CHONDROITIN DRUG COMPLEXES

[75] Inventors: Alan G. Walton, Norwalk, Conn.;
Randall V. Sparer, Lawrence, Kans.;
Nnochiro Ekwuribe, Detroit, Mich.

[73] Assignee: Valcor Scientific Ltd., New York, N.Y.

[21] Appl. No.: 479,865

[22] PCT Filed: Jun. 30, 1982

[86] PCT No.: PCT/US82/00879
§ 371 Date: Mar. 1, 1983
§ 102(e) Date: Mar. 1, 1983

[87] PCT Pub. No.: WO83/00150
PCT Pub. Date: Jan. 20, 1983

Related U.S. Application Data

[63] Continuation-in-part of Ser. No. 279,724, Jul. 2, 1981, abandoned.

[51] Int. Cl.³ .................. A61K 31/70; C08B 37/08
[52] U.S. Cl. .................. 424/180; 536/6.4;
536/54; 536/118; 536/17.2; 536/17.3
[58] Field of Search .......... 536/6.4, 54, 17.2, 17.3, 536/118; 424/180

[56] References Cited

U.S. PATENT DOCUMENTS 4,105,760 8/1978 Szejtli et al. .................. 536/18

FOREIGN PATENT DOCUMENTS 4317566 7/1943 Japan .
1305807 2/1973 United Kingdom .

OTHER PUBLICATIONS

Thesis Entitled "The Synthesis and Characterization of Crosslinked Chondroitin-4-Sulfate Hydrogels: Potential Biomaterials", by Randall V. Sparer, Publicly Available Apr. 4, 1980.
Moersdorf, Chemical Abstracts, 80, 141061 (1974).

Primary Examiner—Ethel G. Love
Attorney, Agent, or Firm—Barnes & Thornburg

[57] ABSTRACT

A chondroitin or a chondroitin sulfate covalently or ionically bonded to a drug substance of the group consisting of chloramphenicol, methotrexate, adriamycin, vinblastine, vincristine, vindesine, 6-mercaptopurine, 5-fluorouracil, the penicillin antibiotics, the cephalosporin antibiotics, and the 1-oxacephalosporin antibiotics to form a prodrug which, when injected into animal tissue, undergoes natural conversion in the physiological environment to provide controlled release of the drug or an active drug complex.

21 Claims, 1 Drawing Figure

CHONDROITIN REPEATING UNIT

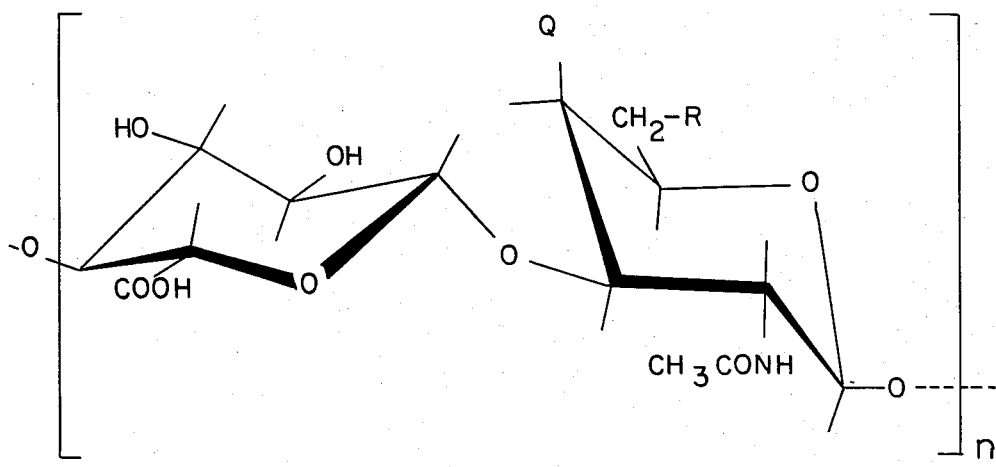
CHONDROITIN REPEATING UNIT

CHONDROITIN DRUG COMPLEXES

This application is a continuation-in-part of our previous application Ser. No. 279,724, filed July 2, 1981, now abandoned.

Many clinical situations exist in which it is advisable, sometimes necessary, to administer a drug in a controlled manner such that the concentration in the tissues of the patient is high enough to be effective but not so high as to cause toxic or other undesirable side effects. The rate of drug release can be controlled in a variety of ways, such as by encapsulation in a material which dissolves slowly in the body fluids, by entrapment in a bolus or matrix from which the drug diffuses slowly, or by conversion into a so-called "prodrug," in which the drug is bound with another substance into a substantially inactive compound or complex and is gradually released by physiological action when injected into the tissues of the patient.

The present invention relates to a novel class of prodrugs in which the drug substance is bonded ionically or covalently to a glycosaminoglycan of the class of the chondroitins, and to the use of such prodrugs in the treatment of animal and human patients.

Danishefsky and Siskovic, *Carbohydrate Research*, 16, 199 (1971), while studying the structure-function implication of the glycosaminoglycans, found that the amino function of certain amino acids can be covalently linked to the carboxyl group of a glycosaminoglycan. This is, of course, a conventional amidation; and while a similar reaction is employed in making some of the substances of the present invention, Danishefsky and Siskovic did not make, or suggest the possibility of making, a prodrug.

Mill et al U.S. Pat. No. 4,003,792 teaches that proteins may be bound to acid polysaccharides of plant origin, specifically alginic acid, pectic acid, celluronic acid, and carageenan. Such polysaccharides are food carbohydrates, alien to the blood and tissues of animals, and are clearly distinct both chemically and physiologically from the chondroitins used in the present invention. While Mill et al indicate that their complexes may be used for preparing antisera and for slow release of antisera, they do not describe how slow release of antisera can be achieved. In contrast, the chondroitin complexes of the present invention are compatible with animal blood and tissue and are normally cleaved by body metabolism to release the active drug.

Yannas and Burke U.S. Pat. Nos. 4,060,081 and 4,059,572 use the ionic properties of mucopolysaccharides (an older term essentially coextensive with the glycosaminoglycans) to flocculate or complex ionically with proteins. For example, an artificial skin formulation was prepared from chondroitin sulfate and collagen.

Heparin (a glycosaminoglycan) is very effective in slowing the clotting of blood, but is relatively short-acting when administered. A variety of derivatives have therefore been made to delay its absorption and prolong its pharmacological action. Thus, Mardiguian and Fournier U.S. Pat. No. 3,835,112 esterifies the hydroxyl groups of heparin with long chain fatty acids to give insoluble complexes which slowly regenerate the active soluble heparin upon cleavage of the ester bond. Bernasconi et al (*G. Ital. Chemioter.*, 3, 79 (1956)) react heparin with tetracycline to produce a slowly soluble salt complex with a prolonged payout of heparin.

Laland Norwegian Patent No. 97,467 (1961) prepares a long-acting salt of adrenocorticotropic hormone (ACTH) and hyaluronic acid. The latter, a mammalian polyuronide, is a non-sulfated glycosaminoglycan, and perhaps for this reason the complex shows no autocatalytic effect and no significant amount of fast hydrolysis.

The advantages of using the chondroitins in the preparation of prodrugs lie in the fact that such molecules are found throughout the body, are biocompatible, are not species-dependent, and are metabolically cleaved from the drug substance in prolonged periods ranging from days to months.

In accordance with the present invention, a chondroitin is reacted in a known manner with a drug substance as hereinafter defined to produce a derivative which, upon injection into the body in the form of a solution or finely divided suspension, is metabolically decomposed to release the drug or a drug complex in therapeutically active form. The drug substance is released from the carrier by hydrolysis of the attachment bond in the case of covalently linked prodrugs, either by body fluids or by enzymes, or is released by enzymatic degradation of the chondroitin matrix, or both; or by gradual ionization in the case of ionically linked prodrugs.

The repeating structural unit of the chondroitins is shown in the drawing. In the basic chondroitin structure, both Q and R are hydroxyl. The chondroitins occur most commonly in one of two forms, chondroitin-4-sulfate ("C4S"), in which the hydroxyl at Q is sulfated, and chondroitin-6-sulfate ("C6S"), in which the hydroxyl at R is sulfated. These substances are water-soluble; and depending upon the drug loading and the nature of the drug complex, the prodrug product may be formulated as an aqueous solution or an aqueous colloidal suspension for injection into the patient.

As will be seen from the drawing, a variety of functional groups are available in the chondroitins for covalent bonding (particularly carboxyl, COOH, and hydroxyl, OH) and for ionic bonding (sulfate —OSO$_3$—, and carboxylate, —COO—) with drugs. Covalent bonding can be by way of ester links, —COOY, or amide links, —CONHY, either directly to an appropriate functional group of the drug or by way of a bioacceptable linking substance, e.g., an amino acid or urea. Thus, drugs having the general formula

are suitable for use in the present invention, where X is or can be converted into a carboxyl, hydroxyl, sulfydryl, or amino function; n is an integer at least 1; Y is the residue of the drug molecule—i.e., its characteristic structure exclusive of the reactive function Y; and Y, when plural, may be the same or different groups. Illustrative drugs include pencillin G, pencillin V, ampicillin, carbenicillin, and the whole range of penicillin antibiotics, both natural and synthetic; cephalothin, cephaloridine, cephaloglycin, cephalexin, cephradine, cefazolin, cefamandole, cefaclor, and the whole range of cephalosporin antibiotics, including the 1-oxa, 1-aza, and 1-carbo analogues thereof; chloramphenicol; adriamycin (daunorubicin); methotrexate; vinblastine; vincristine; vindesine; 6-mercaptopurine; 5-fluorouracil; and the like.

Linking substances typically have the general formula $$R^1-Z-R^2$$

where $R^1$ and $R^2$ are or can be converted into carboxyl, hydroxyl, sulfhydryl, and amino functions and may be the same or different, and where Z is an organic group, the whole substance being bio-acceptable—i.e., having no objectionable toxicity or pharmaceutical activity incompatible with the drug substance. Illustrative linking substances include urea, guanidine, glycine, alanine, phenylalanine, lysine, aspartic acid, glutamic acid, trimethylene glycol, 6-aminocaproic acid, thioglycolic acid, and the like.

The reaction of the chondroitin with the drug substance to obtain the novel substances of the present invention is carried out in a known manner, depending upon the functional groups involved.

Where the chondroitin and the drug substance contain a hydroxyl group and a carboxyl group, respectively, the two can be reacted by use of a carbodiimide; or the carboxyl group can be converted to an acid chloride and reacted with the hydroxyl group; or the carboxyl group can be converted to a mixed anhydride and reacted with the hydroxyl group. All of these procedures and the conditions required therein are old and well known in the art. The same procedures can be used when the chondroitin and the drug substance contain a carboxyl group and a hydroxyl group, respectively. In all cases, the product is an ester. Sulfhydryl groups may be reacted in a manner analogous to hydroxyl groups.

When the chondroitin and the drug substance contain a hydroxyl and an amino group, respectively (or vice versa), the reaction can be caused to proceed through formation of a carbamate bond via the activation of the hydroxyl to a chloroformate moiety with subsequent linking to the amine function. The procedure and proper reaction conditions are well known and conventional in the art. Similarly, a carbonate bond may be formed between two hydroxyl groups (on the chondroitin and on the drug).

When the chondroitin and the drug substance contain a carboxyl group and an amino group, respectively (or vice versa), the reaction is one of conventional amide formation under known conditions employing known procedures, eliminating a molecule of water between the two molecules. Alternatively in such a case, the two substances may be reacted ionically in the presence of water to form a product in the nature of an ammonium salt. In the same way, an acid sulfate or an acid sulfonate can be reacted with an amine to form a salt. The amine function of methotrexate, for example, can be converted to the quaternary ammonium form and subsequently complexed ionically with a chondroitin acidic function. Where one or both of the starting materials contains more than one functional group, it may be desirable to protect groups that are not desired to react, in order to avoid obtaining a mixed product. These are techniques which are well known in the art.

Linking molecules can conveniently be employed when the chondroitin and the drug substance do not contain mutually reactive functional groups—for example, when both contain carboxyl and neither contains primary amino, $-NH_2$. In such a case, any substance can be employed as a linking agent which has two functional groups, one capable of reacting with the chondroitin, the other with the drug. To link carboxyl groups, for example, it is convenient to employ urea, guanidine, or a bio-acceptable diamine such as ethylenediamine or trimethylenediamine, reacted first with the chondroitin, then with the drug substance, or vice versa. Linking molecules can also be employed to overcome steric or other chemical problems in a given case.

The reaction products of the present invention are conveniently prepared for administration by dissolving in water or in an isotonic salt solution, or, in cases where the product is less soluble, by comminuting and suspending in water or an isotonic salt solution. In the latter case, the product can also be dissolved in an appropriate organic solvent such as dimethylsulfoxide, dimethylformamide, or the like, diluted with water to form a colloidal suspension, and vacuum stripped or dialyzed against water to remove the organic solvent. The solution or suspension may appropriately contain from about 5 to about 500 mg. of product per milliter as a suitable concentration for injection into the patient, and the volume injected is chosen to provide the desired drug dosage which will, of course, vary with the drug substance.

We have found that the rates of hydrolysis of C4S and C6S drug complexes are similar for a given drug and loading, and exhibit a significant initial amount of fast hydrolysis, even at low loading—an effect not seen with compounds lacking the sulfate moiety. It is thus considered that the sulfates play a major role in the autocatalytic hydrolysis of C4S and C6S drug complexes.

The invention is illustrated by the following specific examples:

EXAMPLE 1

C4S-Chloramphenicol Ester via C4S Acid Chloride

To an anhydrous solution of the free acid of chondroitin-4-sulfate (C4S, 155.5 mg, prepared by ion exchange) and pyridine (0.2 ml) in dimethylformamide (DMF, 35 ml) is added a solution of thionyl chloride (46.5 mg)) in dimethylformamide (1 ml), and the mixture is stirred at 60° C. for 20 minutes. To the resulting solution of C4S acid chloride is added a solution of chloramphenicol (101.3 mg) in DMF (2 ml) and stirring is continued for 21 hours at room temperature. The C4S-chloramphenicol ester prodrug product is then recovered by neutralizing the reaction mixture with dilute sodium hydroxide, dialyzing extensively against water, and lyophilizing, yielding 172.8 mg of the C4S-chloramphenicol ester prodrug.

EXAMPLE 2

C6S-Chloramphenicol Ester via C6S Acid Chloride

In the same way, the chonodroitin-6-sulfate (C6S) chloramphenicol ester prodrug is prepared by reaction of the free acid of C6S (40.5 mg), pyridine (0.1 ml), anhydrous dimethylsulfoxide (DMSO, 8.5 ml), thionyl chloride (3.7 mg in 0.8 ml DMF), and chloramphenicol (20.8 mg in 1 ml DMF), yielding 22.4 mg of purified ester prodrug.

EXAMPLE 3

C4S-Chloramphenicol Ester via C4S Mixed Anhydride

To an anhydrous solution of the free acid of C4S (51.4 mg) in DMF (11 ml) is added pyridine (0.1 ml) and isobutyl chloroformate (11.0 mg in 0.75 ml DMF), and the mixture is allowed to react at 0° C. for 20 minutes. To the resulting solution of C4S mixed anhydride is added a solution of chloramphenicol (27.1 mg in 1 ml DMF) and stirring is continued for 15 minutes at 0° C., then 12 hours at room temperature. The product is isolated as in Example 1 by neutralization/dialysis/lyophilization, yielding 49.1 mg of ester prodrug.

EXAMPLE 4

C6S-Chloramphenicol Ester via C6S Mixed Anhydride

The C6S-chloramphenicol ester product is prepared according to the procedure of Example 3 by reacting C6S (40.5 mg) in DMSO (8 ml) with isobutyl chloroformate (8.7 mg in 0.8 ml DMSO), pyridine (0.1 ml), and chloramphenicol (20.8 mg in 1 ml DMF). Isolation as in Example 1 yields 19.0 mg of C6S-chloramphenicol ester prodrug.

EXAMPLE 5

C4S-Methotrexate Amide via Carbodiimide

To a solution of C4S (10 mg) and methotrexate dimethyl ester trihydrochloride (12 mg) in a 1:1 DMF/H$_2$O solution (3 ml) under nitrogen is added 1-ethyl-3,3-dimethylaminopropyl carbodiimide (EDC, 6 mg). From the reaction product, worked up as in Example 1, is recovered 14.1 mg of the C4S-methotrexate amide prodrug.

EXAMPLE 6

C4S-Adriamycin Amide via Carbodiimide

To a 1:1 (volume) mixture of DMF and water (1 ml) at pH 2 containing the free acid of C4S (5.1 mg) is added adriamycin (6 mg) in 1:1 DMF/H$_2$O (1 ml) with stirring. 1-Ethyl-3,3-dimethylaminopropyl carbodiimide (EDC, 3 mg) in water (0.5 ml) is then added at room temperature with stirring, during which the pH of the mixture rises to 3.75. After 24 hours, the reaction product is neutralized with sodium bicarbonate, dialyzed extensively against water, and lyophilized. The C4S-adriamycin amide prodrug is obtained as 6.5 mg of pure material.

EXAMPLE 7

C6S-Chloramphenicol Ester via Carbodiimide

A solution of C6S (68.9 mg) in water (5 ml) is added to a solution of chloramphenicol (45.3 mg) in DMF (5 ml) and the pH is adjusted to 4.75 with dilute HCl. EDC (26.2 mg) is added and the pH kept at 4.75 for one hour at room temperature. Workup as in Example 6 yields 83.7 mg of C6S-chloramphenicol ester prodrug.

EXAMPLE 8

C4S-Chloramphenicol Ester via Carbodiimide

A solution of the free acid of C4S (123.5 mg) in anhydrous DMF (1.5 ml) is added to a DMF solution (0.2 ml) containing chloramphenicol (22.7 mg) and 4-pyrrolidinopyridine (4-PP, 18.5 mg) acylation catalyst, follwed by dicyclohexyl-carbodiimide (DCC, 13.5 mg) in DMF (0.2 ml), and held at $-8°$ C. for 36 hours. The insoluble dicyclohexylurea by-product is filtered off and discarded. To the filtrate is added 3 volumes of ether. The precipitate is filtered off, washed with ether and air dried, then redissolved in the minimum amount (0.2 ml) of sodium phosphate buffer (1 M, pH=7). The solid is precipitated again, this time with 3 volumes of ethanol, and washed with ether. The solid is again dissolved in phosphate buffer and reprecipitated as above. After a final ether wash and air drying, a yield of 110.4 mg of pure C4S chloramphenicol ester prodrug is obtained.

EXAMPLE 9

C6S-Chloramphenicol Ester via Acid Catalysis

A portion of the free acid of C6S (50.2 mg) is placed in a vacuum oven over P$_2$O$_5$ at 110° C. overnight to remove water of hydration. The total weight loss is 12.5 mg. The dried material is dissolved in anhydrous dimethyl sulfoxide (DMSO, 3 ml) together with chloramphenicol (94.0 mg) and trifluoracetic acid (0.01 ml) to serve as an acid catalyst. The mixture is stirred at 80° C. for 20 hours, then worked up as in Example 1. A yield of 16.4 mg of C6S-chloramphenicol ester prodrug is obtained.

A carboxyl function of a chondroitin can be esterified to an intermediate moiety possessing an alcohol function, for example ethanol, and the chondroitin-ethyl ester can then be transesterified with a hydroxyl group of a drug or an intermediate linking group under acidic conditions. These methods are illustrated in the two following examples.

EXAMPLE 10

C4S-Chloramphenicol Ester by Transesterification

The ethyl ester of C4S is made by the following method. C4S (1.094 g) is suspended in anhydrous DMF (50 ml) at 60° C., and ethyl iodide (2.5 ml, recently distilled) is added. Stirring is continued for 4 days at 60° C., after which the suspension is filtered, the residue washed twice with ether, redissolved in phosphate buffer (1 M, pH=7), and precipitated from 3 volumes of ethanol. The resulting pellet is washed with ether, redissolved in water, and reprecipitated from ethanol to yield 0.958 g of the ethyl ester of C4S.

Transesterification of the ethyl ester of C4S by a hydroxyl function of chloramphenicol is accomplished by adding the ethyl ester of C4S as produced above (57.0 mg) to chloramphenicol (20.2 mg) and trifluoracetic acid (0.001 ml) in anhydrous DMF (5 ml). After 4 days at 60° C., the product is filtered and worked up in Example 1, yielding 43.2 mg of the ester prodrug of chloramphenicol and C4S.

EXAMPLE 11

C4S-Chloramphenicol Ester by Transesterification

An alternative route of making C4S-ethyl ester is to dissolve the free acid of C4S (60.1 mg) in anhydrous DMF (5 ml) and then add DCC (25.9 mg) in DMF (0.3 ml) followed after 10 minutes by sodium ethoxide (29.3 mg). Stirring at room temperature for 18 hours produces a viscous solution. The product is isolated by removal of DMF (40° C. in vacuo) and trituration in ether; yield, 65.0 mg of the ethyl ester of C4S.

Transesterification of the C4S ethyl ester with a hydroxyl function of chloramphenicol is carried out by dissolving the C4S ethyl ester (58.1 mg), chloramphenicol (20.2 mg), and trifluoroacetic acid (0.001 ml) in anhydrous DMF (5 ml). Stirring at 60° C. for 4 days and working up the reaction product mixture as in Example 1 yields 34.2 mg of C4S-chloramphenicol ester prodrug.

EXAMPLE 12

C4S-Methotrexate Ester via Transesterification

The hydroxyl groups of a chondroitin can be used in a transesterification reaction with an ester function of a drug to yield the acylated chondroitin, i.e., the chondroitin ester prodrug. For example, a hydroxyl function of C4S can be reacted with the dimethyl ester trihydrochloride of methotrexate to yield an ester-linked C4S-methotrexate prodrug according to the following procedure.

To a solution of the free acid of C4S (41.6 mg) in anhydrous DMF (10 ml) is added methotrexate dimethyl ester trihydrochloride (27.7 mg) and trifluoroacetic acid (0.001 ml) as acid catalyst. Stirring at 60° C. for 7 days under anhydrous conditions and product isolation as in Example 1 yields 35.4 mg of the C4S-methotrexate ester prodrug.

The hydroxyl functions of a chondroitin can be caused to react with an activated carboxyl group of a drug or an intermediate linking substance to produce an ester bond. Activation of the molecule to be attached to the chondroitin is achieved by well-known standard methods such as by conversion to the acid chloride or mixed anhydride, by use of carbodiimide, or by use of acid catalyzed transesterification methods. These procedures will be elucidated in the following two examples.

EXAMPLE 13

C4S-Penicillin V Ester via Mixed Anhydride

The carboxyl group of phenoxymethyl penicillin (penicillin V) is ester-linked to the hydroxyl group of C4S by the following mixed anhydride procedure. Penicillin V free acid (3.04 g) is dissolved in a cold (5° C.) mixture of DMF (50 ml) and pyridine (0.80 g), and isobutyl chloroformate (1.19 g) is added with stirring. The mixture is held at −10° C. with stirring for 30 minutes. The mixed anhydride reaction product is not isolated, but is added per se to a solution of the free acid of C4S (1.48 g) in DMF at room temperature. After stirring for 6 hours, the C4S-penicillin V ester prodrug is precipitated from solution with an excess of ether, filtered, neutralized with dilute sodium hydroxide, and lyophilized. The yield is 1.14 g of purified product.

While the above scheme employs a mixed anhydride, a symmetrical anhydride can also be used; i.e., by converting penicillin V into its symmetrical anhydride in a known manner.

EXAMPLE 14

C4S-Penicillin V Ester via Carbodiimide

The reaction of the carboxyl group of penicillin V free acid with a hydroxyl group of C4S can be carried out directly by use of a carbodiimide according to the following procedure. Penicillin V free acid (1.41 g) and EDC (0.64 g) are dissolved in anhydrous DMF (50 ml) and added to a solution of C4S free acid (1.79 g) and pyridine (1.5 ml) in DMF (180 ml), after which the mixtue is stirred and held at room temperature for six hours. The product is isolated as described in Example 13, yielding 1.41 g of the C4S-penicillin V ester prodrug.

The ionic (acidic) nature of the chondroitins can be used to form ionic complexes (salts) with drugs or with drugs attached to an intermediate linking molecule that is basic or can be made basic. The following three examples illustrate this concept.

EXAMPLE 15

C4S-Adriamycin Ionic Complex

An aqueous solution (1 ml) of the sodium salt of C4S (5.1 mg) is dropped into an aqueous solution (1 ml) of the hydrochloric acid salt of adriamycin (6 mg). The mixture is stirred at room temperature for 24 hours and subsequently neutralized with a solution of sodium bicarbonate, dialyzed extensively against water, and lyophilized. Obtained is 8.8 mg of the C4S-adriamycin ionic complex.

EXAMPLE 16

C6S-Alanine-Chloramphenicol Ionic Complex

Drugs which do not include a basic moiety (e.g., a quaternary ammonium group) may be derivatized in such a way as to introduce a basic function to complex with the acidic function of a chondroitin to produce an ionic complex. Illustrative of this is the derivatization of the hydroxyl groups of chloramphenicol with the carboxyl group of an intermediate linking group, alanine, to form an ester. The ammonium function of the alanine-chloramphenicol ester is then complexed with a chondroitin to make a polymeric prodrug salt.

The alanine-chloramphenicol ester is synthesized by dissolving chloramphenicol (12.906 g), N-carbobenzoxy-L-alanine (10.003 g), and 4-pyrrolidinopyridine (0.597 g) in anhydrous tetrahydrofuran (THF, 30 ml). A solution of dicyclohexylcarbodiimide (DCC 8.660 g) in THF (15 ml) is added dropwise to the above with stirring at room temperature. After 17 hours, the insoluble dicyclohexylurea by-product is filtered off and the solvent stripped off in vacuo at 40° C. to yield a yellow oil. The oil is taken up in dichloromethane (300 ml) and extracted successively with three 200 ml portions of each of the following in the order named: saline, 5% acetic acid in saline, saturated sodium bicarbonate, and saline. The organic layer is dried over anyhdrous magnesium sulfate and concentrated to about 20 ml. Addition of 30% HBr in acetic acid (40 ml) to this solution under anhydrous conditions at room temperature over a period of 2 hours removes the protective group from the amino function of the alanine. A large excess (450 ml) of anhydrous ethyl ether is added to the solution, causing the hydrobromide salt of the alanine-chloramphenicol ester to precipitate out. Decanting and trituration in ether followed by recrystallization from anhydrous DMF/ether yields 18.693 g of the salt as a hygroscopic white powder. The hydrobromide salt of the alanine-chloramphenicol ester produced above (44.8 mg) in water (0.5 ml) is added dropwise to a stirred aqueous (1 ml) solution of C6S (29.9 mg) at room temperature. After 4 hours, the mixture is worked up as in Example 1 to yield 38.7 mg of the C6S-alanine-chloramphenicol prodrug.

EXAMPLE 17

C4S-Alanine-Chloramphenicol Ionic Complex

Reaction of C4S (29.8 mg) and alanine-chloramphenicol hydrobromide (44.5 mg) according to the procedure of Example 16 yields 35.2 mg of the C4S-alanine-chloramphenicol prodrug.

EXAMPLE 18

C4S-Urea-Penicillin V

The carboxyl group of penicillin V is amide-linked to a glycosaminoglycan through the amine function of urea as an intermediate linking molecule according to the following procedure. C4S (821.5 mg) and urea (757.8 mg) are dissolved in water (15 ml) at pH 4.75. EDC (434.9 mg) is added and the pH kept at 4.75 for 5 hours at room temperature. The C4S urea amide-linked intermediate is isolated by dialysis and lyophilization. A portion of the C4S-urea (251.5 mg) and penicillin V potassium salt (410.5 mg) are dissolved in water (15 ml) and the pH is adjusted to 6.0. EDC (209.0 mg) is added and the same pH maintained for 5 hours, after which the mixture is worked up as in Example 1, yielding the C4S-urea-pencillin V prodrug.

EXAMPLE 19

C6S-6-Aminocaproic Acid-Chloramphenicol

Long-chain linking molecules containing appropriate functional groups on both ends of the molecule are especially useful in linking a drug with a chondroitin when the point of attachment on the drug is sterically hindered. Drug and linker may be attached in high yield, followed by reaction with the chondroitin.

As an example of such a linker, 6-aminocaproic acid is attached to chloramphenicol in the same manner as alanine (Example 16). N-carbobenzoxy-6-aminocaproic acid (550.1 mg), chloramphenicol (548.7 mg), and 4-pyrrolidinopyridine (25.4 mg) in dry THF (10 ml) are reacted with DCC (394.4 mg) in dry THF (2 ml); and after 16 hours at room temperature and purification as in Example 16, the oil obtained is reacted with 30% HBr/acetic acid (5 ml) at room temperature for 1 hour. Further purification as before yields 382.0 mg of the ester-linked chloramphenicol-6-aminocaproic acid hydrobromide.

The hydrobromide product thus obtained (292.2 mg) and the sodium salt of C6S (158.9 mg) are dissolved in 2:1 DMF/water (2.5 ml) and the pH is adjusted to 4.75. A solution of EDC (125.2 mg) in 2:1 DMF/water (0.5 ml) is added slowly and the pH kept at 4.75 for three hours with stirring at room temperature. Purification is carried out as in Example 1 to yield 189.4 mg of the chloramphenicol-6-aminocaproic acid-C6S prodrug.

EXAMPLE 20

C6S-Alanine-$^{14}$C-Chloramphenicol

Chloramphenicol, radio-labelled with $^{14}$C at both of its dichloroacetyl functions, is amide-linked through alanine to C6S by the following procedure, generally paralleling Example 16.

The sodium salt of C6S (3.024 g) and the radio-labelled $^{14}$C-chloramphenicol-alanine hydrobromide (prepared as in Example 16, 5.173 g) are dissolved in 2:1 DMF/water (55 ml), and the pH is brought to 4.75. To this solution is added a solution of EDC (2.075 g) in 2:1 DMF/water (10 ml) slowly over a period of 1.5 hours, keeping the pH at 4.75. After an additional 2 hour's stirring at room temperature, the solution is neutralized with dilute sodium hydroxide and then dialyzed extensively against water and lyophilized. Purified C6S-alanine-$^{14}$Cchloramphenicol prodrug is obtained in a 3.890 g yield.

Tests are carried out on the C6S-alanine-$^{14}$Cchloramphenicol prodrug by injection as a solution in sterile saline (145 mg/ml) into the flanks of 8 white female rats weighing from 0.3 to 0.4 kg each. The prodrug contains 18.6% by weight of chloramphenicol, and the injection volumes (averaging about 2.5 ml) are chosen to produce a dosage equivalent to 200 mg of chloramphenicol per kg of rat body weight and a radioactivity dosage of 0.50 µCi per kg. Urine and feces are collected and counted for radioactivity. The results are as follows:

| Days After Injection | Cumulative % of Drug Released |
| --- | --- |
| 0.8 | 34.4 |
| 1.3 | 68.6 |
| 1.8 | 81.4 |
| 2.2 | 87.1 |
| 2.8 | 89.1 |
| 3.3 | 90.5 |
| 3.9 | 91.9 |
| 5.0 | 93.8 |
| 6.0 | 95.0 |
| 7.0 | 96.0 |

In order to test the efficacy of the prodrug, blood samples (2 ml) are taken from two of the rats and assayed for antibiotically active chloramphenicol against Sarcina lutea (ATCC 9341) by the method described in 21 Code of Federal Regulations, Subpart D, paragraphs 436.100 to 436.105, inclusive, revised Apr. 1, 1976. When measured 23 hours after injection, the prodrug shows a plasma chloramphenicol concentration of 17.5 µg/ml by microbiological assay and 390 µg/ml by radioactive counting. In contrast, rats injected with free $^{14}$C-Chloramphenicol show a plasma concentration 5 5 hours after injection of 37.5 µg/ml by microbiological assay and 325 µg/ml by radioactive counting; and the drug is completely cleared from the plasma at the end of 12 hours.

The prodrug itself, when tested by microbiological assay, has an activity equivalent to only 1.2 weight-% of chloramphenicol.

EXAMPLE 21

C4S-Alanine-$^{14}$C-Chloramphenicol

The procedure of Example 20 is repeated with the sodium salt of C4S (3.016 g) and radioactive chloramphenicol-alanine hydrobromide (5.133 g) in 2:1 DMF/water (55 ml), and a solution of EDC (2.074 g) in 2:1 DMF/water (10 ml), yielding 3.894 g of purified C4S-alanine-$^{14}$C-chloramphenicol prodrug containing 19.4% by weight of chloramphenicol. The prodrug is tested by injection into seven white female rats in the equivalent dosages and according to the procedure of Example 20. The results are as follows:

| Days After Injection | Cumulative % of Drug Released |
| --- | --- |
| 0.7 | 35.6 |
| 1.3 | 58.7 |
| 1.7 | 76.7 |
| 2.2 | 82.9 |
| 2.8 | 86.6 |
| 3.3 | 88.2 |
| 3.9 | 89.7 |
| 5.0 | 91.6 |
| 6.0 | 93.0 |
| 7.0 | 94.2 |

Blood samples drawn from two of the rats at the end of 22.5 hours show a plasma concentration of 22.5 µg/ml by microbiological assay and a concentration of 485 µg/ml by radioactive counting. The prodrug itself, when subjected to microbiological assay, shows an activity equivalent to only 1.5 weight-% of chloramphenicol.

The rate of release of the drug from the chondroitin or from the linking substance, if used, is dependent on the type of bond(s) chosen for the linkage(s). Thus, although enzymatic mechanisms must be considered and may be controlling in some instances, the release rates of the chondroitin prodrug formulations are ordinarily expected to follow their order of hydrolytic stability. Therefore, ester hydrolyzes faster than amide, etc. The following two examples illustrate this concept.

EXAMPLE 22

Drug Release Rate From C6S-Alanine-Chloramphenicol

In vitro hydrolysis of a prodrug sample in a "physiological" solution can be an effective guide in predicting the release behavior of the prodrug in vivo.

A C6S-alanine-chloramphenicol prodrug synthesized according to the procedure outlined in Example 20 and assaying 5.0% chloramphenicol by weight is dissolved in 4 ml of a "physiological" buffer solution containing 0.15M NaCl and 0.05M Tris buffer, pH 7.4. The resulting solution is placed in a small diameter dialysis tube (to retain the prodrug yet allow free drug to readily pass) and dialyzed at 37° C. against the same physiological buffer solution (81 ml). Ultraviolet analysis of the dialysate at 274 nm gives the following results:

| Days | % of Dose Released |
| --- | --- |
| 0.1 | 6.6 |
| 0.9 | 22.5 |
| 2.2 | 41.0 |
| 3.8 | 50.0 |
| 9.1 | 70.2 |
| 15.1 | 81.8 |

EXAMPLE 23

C4S-Methotrexate Ionic Complex

Methotrexate is ionically bound to C4S by the following method. A solution of methotrexate dimethyl ester (210 mg) in DMF (1 ml) is added slowly to a stirred solution of C4S sodium salt (102.8 mg) in water (2 ml) at room temperature. After ten minutes, the pH is slowly raised to 7.0 with 0.5M NaOH and stirring continued for two hours. The reaction product mixture is dialyzed against distilled deionized water, then lyophilized. The yield is 201 mg of the ionic product.

We claim:

1. A prodrug consisting essentially of chondroitin-4-sulfate or chondroitin-6-sulfate covalently or ionically bonded to a pharmaceutically active substance of the group consisting of chloramphenicol, methotrexate, adriamycin, vinblastine, vincristine, vindesine, 6-mercaptopurine, 5-fluorouracil, the penicillin antibiotics, the cephalosporin antibiotics, and the 1-oxacephalosporin antitiotics and having the property, when injected into animal tissue, of undergoing natural conversion in the physiological environment to provide controlled release of the pharmaceutically active substance or an active complex thereof.

2. A prodrug as in claim 1 wherein said pharmaceutically active substance is chloramphenicol.

3. A prodrug as in claim 1 wherein said pharmaceutically active substance is a penicillin antibiotic.

4. A prodrug as in claim 1 wherein said pharmaceutically active substance is a cephalosporin antibiotic.

5. A prodrug as in claim 1 wherein said pharmaceutically active substance is adriamycin.

6. A prodrug as in claim 1 wherein said pharmaceutically active substance is methotrexate.

7. A prodrug as in claim 1 wherein said pharmaceutically active substance is vinblastine.

8. A prodrug as in claim 1 wherein said pharmaceutically active substance is vincristine.

9. A prodrug as in claim 1 wherein said pharmaceutically active substance is vindesine.

10. A prodrug as in claim 1 wherein said pharmaceutically active substance is 6-mercaptopurine.

11. A prodrug as in claim 2, said prodrug being chondroitin-4-sulfate chloramphenicol ester.

12. A prodrug as in claim 2, said prodrug being chrondroitin-6-sulfate chloramphenicol ester.

13. A prodrug as in claim 6, said prodrug being chondroitin-4-sulfate methotrexate amide.

14. A prodrug as in claim 6, said prodrug being chondroitin-6-sulfate methotrexate amide.

15. A prodrug as in claim 6, said prodrug being chondroitin-4-sulfate ionically bonded to methotrexate.

16. A prodrug as in claim 6, said prodrug being chondroitin-6-sulfate ionically bonded to methotrexate.

17. A prodrug as in claim 5, said prodrug being chondroitin-4-sulfate adriamycin amide.

18. A prodrug as in claim 5, said prodrug being chondroitin-6-sulfate adriamycin amide.

19. A prodrug as in claim 3, said prodrug being chondroitin-4-sulfate penicillin V ester.

20. A prodrug as in claim 5, said prodrug being chondroitin-4-sulfate adriamycin ionic complex.

21. A prodrug as in claim 1 wherein said pharmaceutically active substance is 5-fluorouracil.

* * * * *

UNITED STATES PATENT AND TRADEMARK OFFICE
CERTIFICATE OF CORRECTION

PATENT NO. : 4,489,065
DATED : December 18, 1984
INVENTOR(S) : Alan G. Walton et al.

It is certified that error appears in the above-identified patent and that said Letters Patent is hereby corrected as shown below:

Column 2, line 40, change " $-OSO_3-$ " to -- $-OSO_3^-$ --.

Column 2, line 41, change " $-COO-$ " to -- $-COO^-$ --.

Column 7, line 53, change "mixtue" to --mixture--.

Column 9, line 56, change "Cchloramphenicol" to --C-chloramphenicol--.

Column 9, lines 58 and 59, change "Cchloramphenicol" to --C-chloramphenicol--.

Column 10, line 23, change "5 5" to --5.5--.

Signed and Sealed this

Thirteenth Day of August 1985

[SEAL]

Attest:

DONALD J. QUIGG

Attesting Officer  Acting Commissioner of Patents and Trademarks